United States Patent [19]

Milkowski et al.

[11] 3,966,735
[45] June 29, 1976

[54] 1-3-(4-FLUOROBENZOYL)PROPYL-4-SUBSTITUTED PHENOXY ETHYL PIPERAZINE

[75] Inventors: Wolfgang Milkowski, Burgdorf;
Horst Zeugner, Hannover;
Klaus-Wolf von Eickstedt, Berlin;
Werner Stuhmer, Eldagsen, all of Germany

[73] Assignee: Kali-Chemie Aktiengesellschaft, Hannover, Germany

[22] Filed: Mar. 5, 1974

[21] Appl. No.: 448,381

[30] Foreign Application Priority Data
Mar. 12, 1973 Germany............................ 2312171

[52] U.S. Cl. ............................ 260/268 R; 424/250
[51] Int. Cl.² ...................................... C07D 295/08
[58] Field of Search .............................. 260/268 R

[56] References Cited
UNITED STATES PATENTS

| | | | |
|---|---|---|---|
| 2,695,293 | 11/1954 | Swain | 260/268 R |
| 2,695,295 | 11/1954 | Swain | 260/268 R |
| 3,000,892 | 9/1961 | Janssen | 260/268 R |
| 3,637,704 | 1/1972 | Umemoto | 260/268 R |

FOREIGN PATENTS OR APPLICATIONS

| | | | |
|---|---|---|---|
| 2,027,054 | 6/1970 | Germany | 260/268 R |

*Primary Examiner*—Joseph A. Narcavage
*Assistant Examiner*—David E. Wheeler
*Attorney, Agent, or Firm*—Michael J. Striker

[57] ABSTRACT

Piperazine derivatives having the following general formula

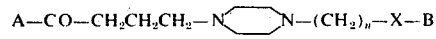

in which $n$ is 2 or 3, X is an oxy or thio radical, and A and B are each a radical of the group consisting of phenyl radicals containing at most three substituents of the group consisting of nitro, trifluoromethyl, halogen, cyano, and alkyl, alkoxy, alkylthio, acyl, and alkylsulfonyl radicals containing at most 6 carbon atoms, and similar cycloalkyl and cycloalkylalkyl radicals, their acid addition salts, processes for their production, and pharmaceutical compositions containing the same. The compounds have a very favorable action on the central nervous system and are effective agents for the treatment of anxiety states, psychoses, emotional disturbances, aggressive tendencies, and can be used generally for the treatment of psychiatrically disturbed and psychoneurotic patients.

4 Claims, No Drawings

1-3-(4-FLUOROBENZOYL)PROPYL-4-SUBSTITUTED PHENOXY ETHYL PIPERAZINE

INTRODUCTION

The present invention pertains to certain compounds which are piperazine derivatives, their acid addition salts, processes for their production, and pharmaceutical compositions containing the same. These piperazine derivatives have the following general formula:

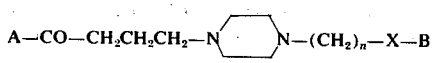

in which formula n is 2 or 3, X is an oxy or thio radical, and A and B are each a radical of the group consisting of phenyl and phenyl radicals having at most three substituents of the group consisting of nitro, trifluoromethyl, halogen, cyano, alkyl, alkoxy, alkylthio, acyl and alkylsulfonyl radicals containing at most six carbon atoms, cycloalkyl, cycoalkoxy, cycloalkylthio, cycloacyl, and cycloalkylsulfonyl radicals having at least 3 and at most 6 carbon atoms and cycloalkylalkyl, cycloalkylalkoxy, cycloalkylalkylthio, cycloalkylacyl, and cycloalkylalkylsulfonyl radicals containing at most 6 carbon atoms.

The methyl, ethyl, n-propyl, isopropyl, n-butyl, sec-butyl, ter-butyl, amyl and hexyl radicals are examples of alkyl radicals; the cyclopentyl, cyclohexyl, and cyclopropyl radicals are examples of cycloalkyl radicals, and cyclopropylmethyl is an example of a cycloalkylalkyl radical. Each of these radicals may be further substituted or combined with other radicals to form the radicals that are specified in the foregoing definition.

BACKGROUND OF THE INVENTION

In our prior application Ser. No. 288,320, filed Sept. 12, 1972, now abandoned which application is incorporated herein by reference, compounds conforming to the foregoing general formula I were disclosed in which compounds X is an oxy radical and A is a phenyl radical or a halogen, lower alkoxy, nitro or alkylamino-substituted phenyl radical and B is an alkoxyphenyl, nitrophenyl, trifluoromethylphenyl, dihalophenyl, dialkylphenyl, halonitrophenyl, haloalkylphenyl, haloalkoxyphenyl, or haloacylphenyl radical.

In German published application No. 2,027,054 are disclosed compounds conforming to the foregoing general formula I in which X is an oxy radical, A is a monohalophenyl or a monoalkoxyphenyl radical, and B is a phenyl, monohalophenyl, or a monoalkylphenyl radical.

The compounds disclosed in the application Ser. No. 288,320 have demonstrated effectiveness as sedatives and also possess analgesic as well as anthihistaminic activity.

SUMMARY OF THE INVENTION

The compounds of the present invention may be produced in accordance with any of the five following reactions or processes:

PROCESS 1

The compounds of the present invention conforming to the general formula I that was specified hereinbefore can be prepared by reacting at a temperature between 0° and 100°C a piperazine derivative having the following general formula:

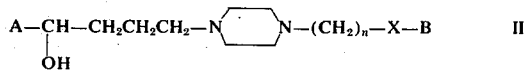

in which A, B, X and n have the same significance as in the general formula I, with an oxidizing agent, such as, for example, an oxidizing agent of the group consisting of manganese dioxide, chromic oxides, alkali-metal chromates and potassium permanganate, in a solvent that is inert with respect to the oxidizing agent. Suitable inert solvents are, for example, benzene, chloroform, pyridine, diethyl ether, and dioxane. The reaction temperature that is used is dependent upon the particular oxidizing agent that is selected. In this reaction, the hydroxyl radical on the carbon atom adjacent to the radical represented by A is oxidized to a carbonyl radical. Such a process is illustrated by Example 1 hereinafter.

PROCESS 2

The compounds of the present invention conforming to the general formula I that was specified hereinbefore can also be prepared from a piperazine derivative having the following general formula:

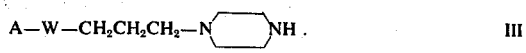

in which A has the same significance as in the general formula I hereinbefore and W represents a carbonyl or an acetalized carbonyl radical having the formula $=C(OR)_2$ or $=C\text{-}O\text{-}R'\text{-}O$ in which formulae R is an alkyl and R' is an alkylene radical.

The foregoing compound having the formula III is reacted in accordance with this process with a phenoxyalkyl or phenylthioalkyl compound having the formula

in which B, X and n have the same significance as in the general formula I hereinbefore and Y is a reactive acid-forming radical such as, for example, a halogen, a 4-toluenesulfonyl or a methanesulfonyl radical. The reaction can be conducted in an inert solvent at a temperature between 50° and 150°C in the presence of an acid-binding substance or the reaction may be conducted without the use of any solvent. If a solvent is not used, the reaction is conducted preferably at a temperature above 100°C. By using an inert solvent such as, for example, benzene, toluene, n-amyl alcohol or methyl isobutyl ketone, the reaction can be conducted suitably at the boiling point of the selected solvent. Suitable acid-binding substances are, for example, tertiary amines such as triethylamine, sodium carbonate, sodium bicarbonate and potassium carbonate, or an excess of the piperazine derivative having the formula III may be added for this purpose. When using an excess of the piperazine derivative having the formula III in which the radical W is a acetalized carbonyl radical, the piperazine derivative that is thus obtained must subsequently by hydrolyzed in the presence of a dilute acid, such as dilute hydrochloric acid, to convert the radical W into a carbonyl radical and thereby produce the desired piperazine derivative having the formula I. This can be readily accomplished by adding the dilute acid directly to the reaction mixture after the condensation of the piperazine derivative having the formula III with the phenoxyalkyl or phenylthioalkyl compound having the formula IV has been completed. Such processes are illustrated by Examples 2 to 4 hereinafter.

PROCESS 3

Piperazine derivatives having the formula I can also be prepared from a piperazine derivative having the formula:

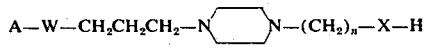    V in which A, X and n have the same significance as in formula I hereinbefore and W is an acetalized carbonyl radical such as described hereinbefore by reacting it with a benzene derivative having the formula

Y — B    VI in which B has the same significance as in formula I and having at least one substituent of the group consisting of nitro, trifluoromethyl or acyl, that means an electronwithdrawing substituent, and Y is an acid-forming halogen radical such as fluorine, chlorine or bromine, in an inert solvent at a temperature between 50 and 200°C and in the presence of a basic condensing agent such as sodium metal, sodium hydride or sodium amide, and after completion of the reaction, deacetalizing the acetalized carbonyl radical by hydrolysis in the presence of an acid such as dilute hydrochloric acid. Inert solvents in which the reaction can be conducted include, for example, dimethyl sulfoxide, N,N-dimethylformamide, benzene, toluene and dioxane. Such processes are illustrated by Examples 5 and 6 hereinafter.

PROCESS 4

The compounds of the present invention conforming to the general formula I can also be prepared by reaction of a piperazine derivative having the following formula:

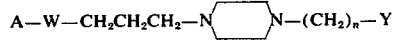    VII in which A and n have the same significance as in formula I hereinbefore, W is a carbonyl or an acetalized carbonyl radical and Y is a reactive acid-forming radical such as, for example, a halogen, a 4-toluenesulfonyl or a methanesulfonyl radical, with an alkali-metal phenoxide or thiophenoxide having the formula

M — X — B    VIII in which X and B have the same significance as in formula I hereinbefore and M is an alkali-metal radical, at a temperature between 50° and 200°C in an inert solvent and, if required, hydrolysis of the acetalized carbonyl radical in the presence of a dilute acid. Inert solvents which were referred to in connection with Process 3 hereinbefore are also suitable for use in this process which is illustrated by Example 7 hereinafter.

PROCESS 5

The compounds of the present invention conforming to formula I can also be prepared by reaction of a phenylcarbonylpropane derivative having the formula

A — W — CH$_2$CH$_2$CH$_2$— Y    IX in which A has the same significance as in formula I hereinbefore, W is a carbonyl or an acetalized carbonyl radical and Y is an acid-forming radical such as a halogen or another of the group of acid-forming radicals that were referred to hereinbefore, with a piperazine derivative having the formula

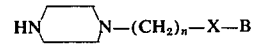    X in which B and n have the same significance as in formula I hereinbefore, at an elevated temperature, generally between 50 and 150°C in the presence of an acid-binding agent such as triethylamine, sodium carbonate, potassium carbonate or an excess of the piperazine derivative having the formula X and, after completion of the condensation reaction, if required, subsequent hydrolysis if the acetalized carbonyl radical in the presence of a dilute acid. The reaction can also be conducted in an inert solvent at the boiling point of the solvent. Suitable inert solvents include methyl isobutyl ketone, n-butanol, toluene and xylene. Such a process is illustrated by Examples 8 and 9 hereinafter. This general process has already been disclosed in our prior application Ser. No. 288,320.

The compounds containing an acetalized carbonyl radical that were referred to hereinbefore, that is, compounds in which the radical represented by W is a carbonyl radical that has been acetalized by condensation with an alcohol or glycol and have the formulae =C(OR)$_2$ and =C-O-R'-O in which R is an alkyl and R' is an alkylene radical, which can be produced in conventional manner, namely, by reaction of the compound containing the carbonyl radical in the presence of an acid with an alcohol, preferably a polyol such as ethylene glycol (1,2-ethanediol), propylene glycol (1,2-propanediol), or trimethylene glycol (1,3-propanediol). In most cases the use of the compound containing the acetalized carbonyl radical promotes a smoother reaction with the result that a higher yield of the desired product is obtained than would be obtained with a compound in which the carbonyl radical is not protected by acetalization. After the reaction has been completed, the acetalized radical can be hydrolyzed to the free carbonyl radical in the presence of dilute hydrochloric acid, and the compounds conforming to the general formula I thereupon precipitate from the reaction mixture in the form of a dihydrochloride salt.

In the foregoing processes, the piperazine derivatives can be recovered from the reaction mixture in which they are formed either directly as the free base by conventional means, or in the form of an acid addition salt which can then be converted to the free base by hydrolysis. To obtain the free base in purer form it is generally advantageous to convert the base to an acid addition salt, such as, for example, the dihydrochloride or dimaleate, which can then be purified more readily than the base itself. The free base can then be converted to any of its nontoxic and pharmaceutically acceptable acid addition salts in conventional manner.

For the preparation of nontoxic acid addition salts of the piperazine derivatives of the present invention, acetic, propionic, diethylacetic, malonic, succinic, fumaric, lactic, tartaric, malic, citric, sulfuric, hydrobromic, orthophosphoric, and methanesulfonic acids may be used, beside hydrochloric and maleic acids. These acid addition salts of the piperazine derivatives as well as the free bases are pharmaceutically acceptable but a particular advantage of the acid addition salts is that they are soluble in water.

DETAILED DESCRIPTION OF THE PREFERRED EMBODIMENTS OF THE INVENTION

The invention is further described in connection with the following examples which are selected solely for purposes of illustration and are not to be construed as limiting the invention.

EXAMPLE 1

1-[3-(4-Fluorobenzoyl)propyl]-4-[2-chloro-4,5-dimethylphenoxy)ethyl]piperazine dihydrochloride To a solution of 2 grams of 1-[4-(4-fluorophenyl)-4-hydroxybutyl]-4-[2-(2-chloro-4,5-dimethylphenoxy)ethyl]piperazine in 40 milliliters of benzene was added 10 grams of manganese dioxide and the mixture was stirred for six hours at room temperature. The mixture was subsequently filtered and the filtrate was evaporated to dryness. The residue was then dissolved in a solution of hydrogen chloride in isopropanol and the crystals of the compound that is specified in the heading were separated from the solution by filtration and recrystallized from ethanol. In this manner, 2 grams of the compound, which had a melting point of 232°–244°C, was obtained.

EXAMPLE 2

1-[3-(4-Fluorobenzoyl)propyl]-4-[2-(2-methyl-5-nitrophenoxy)ethyl]piperazine dihydrochloride A mixture consisting of 29.4 grams of 1-[4-(4-Fluorophenyl)-4,4-ethylenedioxybutyl]-piperazine and 26 grams of 2-(2-methyl-5-nitrophenoxy)ethyl bromide, 11 milliliters of triethylamine, and 500 milliliters of methyl isobutyl ketone was heated under gentle reflux for a period of 5 hours. After cooling, the precipitated solids were separated by filtration and the filtrate was acidified by the addition thereto of an aqueous solution containing 20% by weight of hydrochloric acid with vigorous stirring. The compound that is specified in the heading separated out in the form of crystals which were separated from the solution by filtration, washed with diethyl ether, and recrystallized from ethanol containing 20% by volume of water. In this manner, 25 grams of the compound specified in the heading, having a melting point of 237°–240°C, was obtained.

EXAMPLE 3

1-[3-(4-Fluorobenzoyl)propyl]-4-[2-(2-nitro-4-methylphenoxy)ethyl]piperazine dihydrochloride A mixture consisting of 25 grams of 1-[3-(4-fluorobenzoyl)propyl]piperazine and 26 grams of 2-(4-methyl-2-nitrophenoxy)ethyl bromide, 9.0 grams of sodium bicarbonate and 500 milliliters of n-amyl alcohol was heated under gentle reflux for a period of 5 hours. After cooling, the precipitated solids were separated by filtration and the filtrate was acidified by the addition thereto with vigorous stirring of an aqueous solution containing 20% by weight of hydrochloric acid. Crystals of the compound specified in the heading separated from the solution. The cyrstals were separated from the solution by filtration, washed with diethyl ether and recrystallized from ethanol. In this manner, 15 grams of the compound specified in the heading, which had a melting point of 221°–225°C, was obtained.

EXAMPLE 4

1-[3-(4-Fluorobenzoyl)propyl]-4-[2-(2-methoxy-4-methylphenoxy)ethyl]piperazine dihydrochloride A mixture of 5 grams of 1-[3-(4-fluorobenzoyl)-propyl]-piperazine and 3.5 grams of 2-(4-methyl-2-methoxyphenoxy)ethyl 4-toluenesulfonate was heated in an oil bath at a temperature of 120°C for a period of 2 hours, after which the reaction mixture was permitted to cool. The mixture was neutralized by the addition thereto of an aqueous 10% solution of sodium hydroxide and the solution was then extracted with benzene. After separation from the aqueous phase, the benzene extract was subjected to chromatographic separation in a column filled with chromatographic-grade aluminum oxide granules. The column was then eluted with benzene and the eluate was subjected to vacuum evaporation. The residue was dissolved in methyl isobutyl ketone and the resulting solution was acidified with an aqueous 20%-by-weight solution of hydrochloric acid which was added while the solution was stirred vigorously. Crystals of the compound specified in the heading were separated from the solution. These crystals were then separated from the solution and recrystallized from ethanol. In this manner, 1.9 grams of the compound, which had a melting point of 211°–213°C, was obtained.

EXAMPLE 5

1-[3-(4-Fluorobenzoyl)propyl]-4-[2-(4-methylsulfonylphenoxy)ethyl]piperazine dihydrochloride A solution consisting of 20 grams

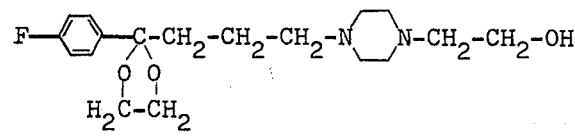

dissolved in 120 milliliters of dimethyl sulfoxide was cooled in an ice bath and 2.2 grams of a dispersion of sodium hydride in oil which contained 75% by weight of sodium hydride was added thereto while the mixture was vigorously stirred. After the end of the evolution of hydrogen from the reaction mixture, 11 grams of 4-(methylsulfonyl)fluorobenzene were added thereto and the mixture was heated for 5 hours at a temperature of 120°C. After the reaction mixture had cooled, it was poured onto 1000 grams of ice, and the resulting mixture was then extracted several times with small portions of chloroform. The chloroform extracts were combined, washed with water, dried by contact with anhydrous sodium sulfate, filtered, and evaporated to dryness. The residue was then dissolved in an ethanolic solution of hydrogen chloride, from which the compound specified in the heading separated. The compound was separated from the solution by filtration and recrystallized from ethanol containing 20% by volume of water. In this manner 9.3 grams of the compound, which had a melting point of 231°–233°C, was obtained.

EXAMPLE 6

1-[3-(4-Fluorobenzoyl)propyl]-4-[2-(4-trifluoromethyl-2-nitrophenoxy)ethyl]piperazine dihydrochloride By substituting an equimolecular proportion of 4-trifluoromethyl-2-nitro-1-chlorobenzene for the 4-(methylsulfonyl)-fluorobenzene that was used in Example 5, and proceeding in the same manner as described therein, the compound that was specified in the heading, having a melting point of 218°–221°C, was obtained.

EXAMPLE 7

1-[3-(4-Fluorobenzoyl)propyl]-4-[2-(4-methyl-2-methoxyphenoxy)ethyl]piperazine dihydrochloride To a solution of 34 grams of 1-[4-(4-Fluorophenyl)-4,4-ethylenedioxybutyl]-4-(2-hydroxy-ethyl)-piperazine that is specified in Example 5 in 200 milliliters of pyridine was added 20 grams of 4-toluenesulfonyl chloride and the mixture was left at room temperature for a period of 15 hours, after which the mixture was poured onto ice and the resulting mixture was extracted with several portions of chloroform. The chloroform extracts were combined, washed with water, dried by contact with anhydrous sodium sulfate, filtered, and the chloroform was then evaporated from the filtrate. The residue was dissolved in 200 milliliters of N,N-dimethylformamide and the solution was slowly added portionwise to a cooled solution of sodium 4-methyl-2-methoxyphenoxide in 50 milliliters of N,N-dimethylformamide and subsequently heated for 24 hours at a temperature of 70°C. After cooling, the mixture was poured onto ice and the resulting mixture was extracted with several portions of chloroform. The chloroform extracts were combined, washed with water, dried by contact with anhydrous sodium sulfate, filtered and the chloroform was then evaporated from the filtrate. The residue was dissolved in a solution of hydrogen chloride in ethanol and the crystals that precipitated were separated by filtration and recrystallized from ethanol. The compound thus obtained, which is referred to by name in the heading of this example, had a melting point of 211°–213°C.

EXAMPLE 8

1-[3-(4-Fluorobenzoyl)propyl]-4-[2-(4-methyl-2-methoxyphenoxy)ethyl]piperazine dihydrochloride A mixture of 25.0 grams of 1-[2-(4-methyl-2-methoxyphenoxy)ethyl]piperazine, 20.1 grams of 3-(4-fluorobenzoyl)propyl chloride, 13.8 grams of potassium carbonate and 10 grams of potassium bromide was heated under gentle reflux for a period of 24 hours. The resulting reaction mixture was filtered while hot and the filtrate after cooling was acidified by adding thereto with stirring a 10% solution of hydrochloric acid, whereupon the compound that is specified in the heading separated. The resulting precipitate was then separated by filtration and recrystallized from a mixture of 80 parts by volume of ethanol and 20 parts by volume of water. In this manner, 15 grams of the salt specified in the heading, having a melting point of 211°–213°C, was obtained.

EXAMPLE 9

1-[3-4-Fluorobenzoyl)propyl]-4-[2-(4-chlorophenylthio)ethyl]piperazine dihydrochloride A mixture of 25.7 grams of 1-[2-(4-chlorophenylthio)-ethyl]piperazine, 24.5 grams of the acetal formed by condensation in the presence of an acid of ethylene glycol with 4-chloro-1-(4-fluorophenyl)-1-butanone, 14 grams of potassium carbonate and 10 grams of potassium bromide in 250 milliliters of methyl isobutyl ketone was heated under gentle reflux for a period of 48 hours. The resulting reaction mixture was filtered while hot and the filtrate after cooling was acidified by adding thereto with stirring a 10% solution of hydrochloric acid, whereupon the compound that is specified in the heading separated. The resulting precipitate was then separated from the solvent by filtration and recrystallized from ethanol. In this manner, 30 grams of the salt specified in the heading, having a melting point of 241°–243°C, was obtained.

Additional Examples of compounds which were prepared in accordance with one of the processes described in the foregoing examples are included in the table which follows.

| Ex. No. | Compound | Melting point of Dihydrochloride of compound, °C |
|---|---|---|
| 10 | 1-[3-(4-Fluorobenzoyl)propyl]-4-[2-(3-acetylphenoxy)ethyl]piperazine | 200–202 |
| 11 | 1-[3-(4-Fluorobenzoyl)propyl]-4-[2-(4-cyanophenoxy)ethyl]piperazine | 238–241 |
| 12 | 1-[3-(4-Fluorobenzoyl)propyl]-4-[2-(4-methylmercaptophenoxy)ethyl]-piperazine | 205–210 |
| 13 | 1-[3-(4-Fluorobenzoyl)propyl]-4-[2-(2-chloro-4-acetylphenoxy)ethyl]-piperazine | 228–234 |
| 14 | 1-[3-(4-Fluorobenzoyl)propyl]-4-[2-(4-propionyl-2-chlorophenoxy)ethyl]piperazine | 252–256 |
| 15 | 1-[3-(4-Fluorobenzoyl)propyl]-4-[2-(2-methyl-4-acetylphenoxy)ethyl]piperazine | 230–237 |
| 16 | 1-[3-(4-Fluorobenzoyl)propyl]-4-[2-(2-ethyl-4-acetylphenoxy)ethyl]piperazine | 235–240 |
| 17 | 1-[3-(4-Fluorobenzoyl)propyl]-4-[2-(3,-4-dimethoxyphenoxy)ethyl]piperazine | 225–230 |
| 18 | 1-[3-(4-Fluorobenzoyl)propyl]-4-[2-(4-chloro-2,5-dimethylphenoxy)ethyl]piperazine | 232–240 |
| 19 | 1-[3-(4-Fluorobenzoyl)propyl]-4-[2-(4-chloro-3,5-dimethylphenoxy)ethyl]piperazine | 242–247 |
| 20 | 1-[3-(4-Fluorobenzoyl)propyl]-4-[2-(2,-3-dichloro-4-acetylphenoxy)ethyl]piperazine | 254–260 |
| 21 | 1-[3-(4-Fluorobenzoyl)propyl]-4-[2-(4-methylphenylthio)ethyl]-piperazine | 218–220 |
| 22 | 1-[3-(4-Fluorobenzoyl)propyl]-4-[2-(4-nitrophenylthio)ethyl]piperazine | 237–244 |
| 23 | 1-[3-(4-Fluorobenzoyl)propyl]-4-[2-(4-fluorophenylthio)ethyl]piperazine | 215–218 |

UTILITY OF THE COMPOUNDS OF THE INVENTION

The compounds that are disclosed in this application have a very favorable action on the central nervous system. They are effective agents for the treatment of anxiety states, psychoses, emotional disturbances, aggressive tendencies, and can be used generally for the treatment of psychiatrically disturbed and psychoneurotic patients.

The piperazine derivatives disclosed herein as well as their pharmaceutically acceptable acid addition salts can be used as medicaments in the form of pharmaceutical compositions that are suitable for peroral or parenteral administration, in which the compounds are admixed or combined with inert inorganic or organic vehicles such as, for example, water, gelatin, lactose, starches, magnesium stearate, talc, vegetable oils, gums, glycols, and petrolatum. The pharmaceutical composition may be dispensed in the form of a solid, such as, for example, tablets, pills, and capsules, or in the form of a liquid such as solutions, elixirs, suspensions, or emulsions. If necessary, the compositions are sterilized and other substances such as preservatives, stabilizers, wetting or emulsifying agents, buffer salts, or salts which modify the osmotic pressure, are added. Other therapeutically effective substances may also be included in such pharmaceutical compositions.

The therapeutic dosages of the compounds disclosed herein is dependent upon the age, weight, and condition of the patient. Preferably the dose will range between 1 and 200 milligrams per kilogram body weight per day. These dosages can be given once per day or can be divided up into smaller unit doses taken at specified intervals during the day. When administered parenterally, the doses required are smaller than those which would normally be required for peroral administration.

The results of pharmacological investigations that are referred to hereinafter serve to illustrate the specific effectiveness of the compounds. These investigations have proved that the toxicity of the new compounds is considerably lower than that of known substances that are used for the same therapeutic purposes.

The compounds were subjected to the following pharmacological tests or determinations:

1. Acute toxicity: The acute toxicity is determined by a single oral administration to fasting white mice of the NMRI strain. The minimum lethal dose ($LD_{50}$) is computed in accordance with the method described by J.T. Litchfield and F. Wilcoxon in Journal of Pharmacology and Experimental Therapeutics, vol. 96, page 99 (1949).

2. Test of prolongation of narcosis induced by hexobarbital: In accordance with this test, the test substance is administered perorally to a mouse. After an interval of 30 minutes, a dose of 65 milligrams of hexobarbital per kilogram of body weight is administered intravenously. The result is reported as the dose of the test compound that was required to double the period of sleeping time that was induced by the hexobarbital.

3. Test of sedative effectiveness: In this test is measured the period of narcosis that is induced by the test substance following a period of narcosis induced by hexobarbital. A dose of 100 milligrams of hexobarbital per kilogram of body weight is administered intraperitoneally to female mice of the NMRI strain. As soon as the mouse revives or awakens from the narcosis induced by the dose of hexobarbital, a measured dose of the test substance is administered intraperitoneally. The period between the administration of the test substance and the second revival of the mouse is then noted. From the length of this second period is calculated the dose of the test substance that was required to induce sleep for a period of 30 minutes and this dose is referred to as the effective sedative dose ($ED_{50}$).

4. Squirrel-cage test for determining effect of drugs on motility: The test substance is administered perorally to female mice of the NMRI strain that had previously not been exercised in a squirrel cage. Twenty mice are placed into the revolving cylinder of the squirrel cage and they are allowed to run freely therein. The number of revolutions through which the cylinder in the squirrel cage spins every 15 minutes is noted during the course of an extended period of 5 hours, when the test is discontinued. The average of the number of revolutions per minute is calculated and represented on a graph. These values are then compared with standard results obtained in the same test with mice to whom 21.8 milligrams of Chlordiazepoxide per kilogram of body weight had been administered perorally and the results are reported in milligrams per kilogram of body weight.

In the table which follows are listed the values obtained in units of milligrams per kilogram as a result of the foregoing tests in which the named substances in the following list that are identified also by number were tested.

1) 1-[3-(4-Fluorobenzoyl)propyl]-4-[2-(4-cyanophenoxy)ethyl]-piperazine dihydrochloride. (Example 11)
2) 1-[3-(4-Fluorobenzoyl)propyl]-4-[2-(4-chlorophenylthio)-ethyl]piperazine dihydrochloride. (Example 9)
3) 1-[3-(4-Fluorobenzoyl)propyl]-4-[2-(4-propionyl-2-chlorophenoxy)ethyl]piperazine dihydrochloride. (Example 14)
4) 1-[3-(4-Fluorobenzoyl)propyl]-4-[2-(4-methyl-2-nitrophenoxy)ethyl]piperazine dihydrochloride. (Example 3)
5) 1-[3-(4-Fluorobenzoyl)propyl]-4-[2-(4-methyl-2-methoxyphenoxy)ethyl]piperazine dihydrochloride. (Example 4)
6) 1-[3-(4-Fluorobenzoyl)propyl]-4-[2-(5-nitro-2-methylphenoxy)ethyl]piperazine dihydrochloride. (Example 2)
7) 1-[3-(4-Fluorobenzoyl)propyl]-4-[2-(4-methylsulfonylphenoxy)ethyl]piperazine dihydrochloride. (Example 5)
8) 1-[3-(4-Fluorobenzoyl)propyl]-4-[2-(4-nitrophenylthio)-ethyl]piperazine dihydrochloride. (Example 22)

| Substance No. | Acute toxicity $LD_{50}$ mg/kg | Narcotic prolongation effect (Test 2) mg/kg | Effective sedative dose $ED_{50}$ (Test 3) mg/kg | Squirrel cage motility test versus 21.5 mg/kg chlordiazepoxide (Test 4) |
|---|---|---|---|---|
| 1 | 215 | 10 | 21.5 | 0.7 |
| 2 | >1470 | 20 | 30 | >10 |
| 3 | 860 | 20 | 14 | 1.5 |
| 4 | 1720 | 20 | 46 | |
| 5 | 458 | 46 | 7 | 3.2 |

-continued

| Substance No. | Acute toxicity LD$_{50}$ mg/kg | Narcotic prolongation effect (Test 2) mg/kg | Effective sedative dose ED$_{50}$ (Test 3) mg/kg | Squirrel cage motility test versus 21.5 mg/kg chlordiazepoxide (Test 4) |
|---|---|---|---|---|
| 6 | >1470 | 32 | 23 | |
| 7 | 825 | 46 | 30 | 6.8 |
| 8 | 499 | 6 | 30 | 6.8 |

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A compound having the formula

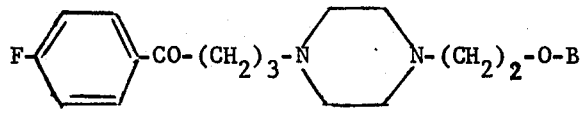

in which B is a 2-chloro-4-alkanoylphenyl radical, the alkanoyl moiety of which has at least 2 and at most 4 carbon atoms, and pharmaceutically acceptable acid addition salts thereof.

2. A compound as defined in claim 1 in which B is a 2-chloro-4-acetylphenyl or 2-chloro-4-propionylphenyl radical.

3. A compound as defined in claim 1 which is 1-[3-(4-fluorobenzoyl)propyl]-4-[2-(2-chloro- 4-acetylphenoxy)-ethyl]piperazine.

4. A compound as defined in claim 1 which is 1-[3-(4-fluorobenzoyl)propyl]-4-[2-(2-chloro-4-propionylphenoxy)ethyl]piperazine.

* * * * *